(12) United States Patent
Badenhorst

(10) Patent No.: US 10,517,558 B2
(45) Date of Patent: Dec. 31, 2019

(54) ANKLE IMAGING ACCESSORY

(71) Applicant: Stellenbosch University, Stellenbosch (ZA)

(72) Inventor: De la Rey Hertzog Scheepers Badenhorst, Bellville (ZA)

(73) Assignee: Stellenbosch University, Stellenbosch (ZA)

( * ) Notice: Subject to any disclaimer, the term of this patent is extended or adjusted under 35 U.S.C. 154(b) by 258 days.

(21) Appl. No.: 15/609,359

(22) Filed: May 31, 2017

(65) Prior Publication Data
US 2017/0347977 A1    Dec. 7, 2017

(30) Foreign Application Priority Data

Jun. 1, 2016   (ZA) .................................. 2015/08773

(51) Int. Cl.
*A61B 6/04* (2006.01)
*A61B 6/00* (2006.01)

(52) U.S. Cl.
CPC ............ *A61B 6/505* (2013.01); *A61B 6/0421* (2013.01); *A61B 6/582* (2013.01)

(58) Field of Classification Search
CPC .. A61B 6/00; A61B 6/04; A61B 6/505; A61B 6/582; A61B 6/0492

USPC ......................................... 378/204, 205, 208
See application file for complete search history.

(56) References Cited

U.S. PATENT DOCUMENTS

| | | | |
|---|---|---|---|
| 7,527,428 B2* | 5/2009 | Riley ....................... | A61B 6/04 378/177 |
| 7,822,462 B2* | 10/2010 | Elias ........................ | A61B 6/04 378/20 |
| 2017/0042465 A1* | 2/2017 | Coelho Do Sameiro Espregueira Mendes .................... | A61B 6/04 |

OTHER PUBLICATIONS

Donken et al., "Use of an Acrylic Mold for Mortise View Improvement in Ankle Fractures: A Feasibility Study" The Jorunal of Foot & Ankle Surgery, vol. 50 (2011) pp. 525-528.

* cited by examiner

*Primary Examiner* — Jurie Yun
(74) *Attorney, Agent, or Firm* — Remenick PLLC

(57) ABSTRACT

An ankle imaging accessory is provided by the present invention, particularly an ankle positioning device to facilitate the taking of X-ray views of a patient who had sustained an ankle fracture. The ankle imaging accessory is made from an X-ray translucent material and includes heel supports on which heels of a patient can locate. A pair of spaced apart stops defines the limits of an arc on which a foot pivoting on the heel support can move.

7 Claims, 4 Drawing Sheets

500
ANKLE IMAGING ACCESSORY

CROSS REFERENCE TO RELATED APPLICATIONS

This application claims priority from South African provisional patent application number 2015/08773, which has an effective filing date of 1 Jun. 2016, and which is entirely incorporated by reference herein.

FIELD OF THE INVENTION

This invention relates to an ankle imaging accessory and in particular to an ankle positioning device to facilitate the taking of X-ray views thereof.

BACKGROUND TO THE INVENTION

Correct X-ray views is important in the management of fractured ankles and in determining the treatment choice for the ankle fracture. There are generally three X-ray views used to evaluate an ankle fracture which are the anteroposterior (AP) view or the mortise view, the lateral or side view, and the calcaneal or back view of the ankle. It has been shown that the mortise view is the most reliable for use in the assessment of ankle congruity where the foot is internally rotated approximately 20° while the foot is maintained at a 90° angle relative to the leg. In such position, the medial and lateral malleoli of the leg are projected without the projection of the talus over the medial and lateral malleolus.

Obtaining accurate mortise views usually depend on the experience of radiographers and it is not uncommon for incorrect views to be sent to a surgeon. These errors are usually as a result of the variability associated with routine, freehand positioning of the ankle by the radiographers. In such cases, these incorrect views are sent for repeat X-rays until adequate views for evaluation are obtained. This causes unnecessary radiation exposure to a patient and usually involves additional costs.

A device is known which attempts to alleviate the above mentioned problem by maintaining an ankle in an optimal standardized position while procuring the mortise radiographic image. This device is disclosed in The Journal of Foot and Ankle Surgery by Donken, Christian CMA, et al., with title "Use of an Acrylic Mold for Mortise View Improvement in Ankle Fractures: A Feasibility Study". This device comprises a transparent acrylic positioning jig or mould consisting four 4-mm-thick panels of radiolucent acrylic material (transparent polymethyl methacrylate). The first panel is a rectangular base with the second panel extending from a short side thereof. The first and second panels support the two remaining panels which diverge from the middle of the base at −25° and 25° angles relative to a vertical and longitudinal plane through the base.

The acrylic jig is used to position an injured foot of a patient lying on a radiographic examination table in the supine position with the ankle maintained at a 90° angle relative to the leg and with the foot rotated inwardly at about 25°. An X-ray image of the ankle may then be captured. The acrylic jig does not provide for the taking of the AP mortise views at different inwardly rotated angular displacements of the foot at specific angles of less than the 25° and also does not provide for the taking of the calcaneal view of the ankle. Further, the second foot of the patient has to be placed independently in the acrylic jig in a separate procedure and X-ray images of the second foot may then be captured for comparative purposes. The divergent panels of the jig also extend up an appreciable height of the leg, namely about 500 mm.

There is a need for an ankle imaging accessory that can be used by a radiographer to obtain better and more accurate mortise views of an ankle conveniently and which alleviates the above mentioned problems at least to some extent.

In the remainder of the specification the term "X-ray translucent material" should be construed widely and shall include all materials that would allow an X-ray image to be taken therethrough, including X-ray translucent material, X-ray transparent material, radiolucent structural materials, and the like.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided an ankle imaging accessory comprising a pair of heel supports on which heels of a pair of feet can locate, the heel supports extending substantially normally from a wall for supporting the heels, a pair of spaced apart stops extending from the wall in association with each heel support and which define the limits of an arc on which a foot pivoting on the heel support can pivot, wherein the arc has a maximum size of 25° in at least an inward direction relative to a centreline through a heel support that is parallel to a sagittal plane through the ankle imaging accessory, and wherein the accessory is made from an X-ray translucent material.

Further features of the invention provide for calibrations indicating selected angular displacements of a foot between the stops to be provided on the wall; and for a calibration indicating a calcaneal view to be provided on or near the heel support.

Yet further features of the invention provide for a heel pivoting device to be pivotally secured to the wall at each heel support; and for the heel pivoting device to be pivotable between its associated pair of stops.

Still further features of the invention provide for the ankle imaging accessory to include a sphere of an X-ray opaque material of known diameter; for the sphere to be secured internally of the accessory; and for the diameter of the sphere to be depicted on the accessory.

In order that the invention may be more fully understood an extended description of two embodiments thereof follows with reference to the accompanying drawings.

DETAILED DESCRIPTION WITH REFERENCE TO THE DRAWINGS

The invention described in this application provides an ankle imaging accessory and in particular provides an ankle positioning device to facilitate the taking of X-ray views of an ankle of a patient. The ankle imaging accessory is made from an X-ray translucent material that allows X-ray views to be taken therethough, and has a pair of heel supports on which heels of a pair of feet of the patient can locate. The heel supports extend substantially normally from a wall which supports the heels of the patient. A pair of spaced apart stops extend from the wall in association with each heel support and defines the limits of an arc on which a foot pivoting on the heel support can move. The arc may have a maximum size of 25° in at least an inward direction relative to a centreline through a heel support that is parallel to a sagittal plane through the ankle imaging accessory.

Calibrations which indicate selected angular displacements of a foot between the stops may be provided on the wall, and a calibration which indicates a calcaneal view may be provided adjacent each heel support. A sphere of material that is opaque to X-rays and of known diameter, for example 30 mm, may be secured internally of the accessory. The known diameter of the sphere may be depicted on the accessory and may be used to ascertain an ankle displacement of a foot of a patient.

Figure 1:
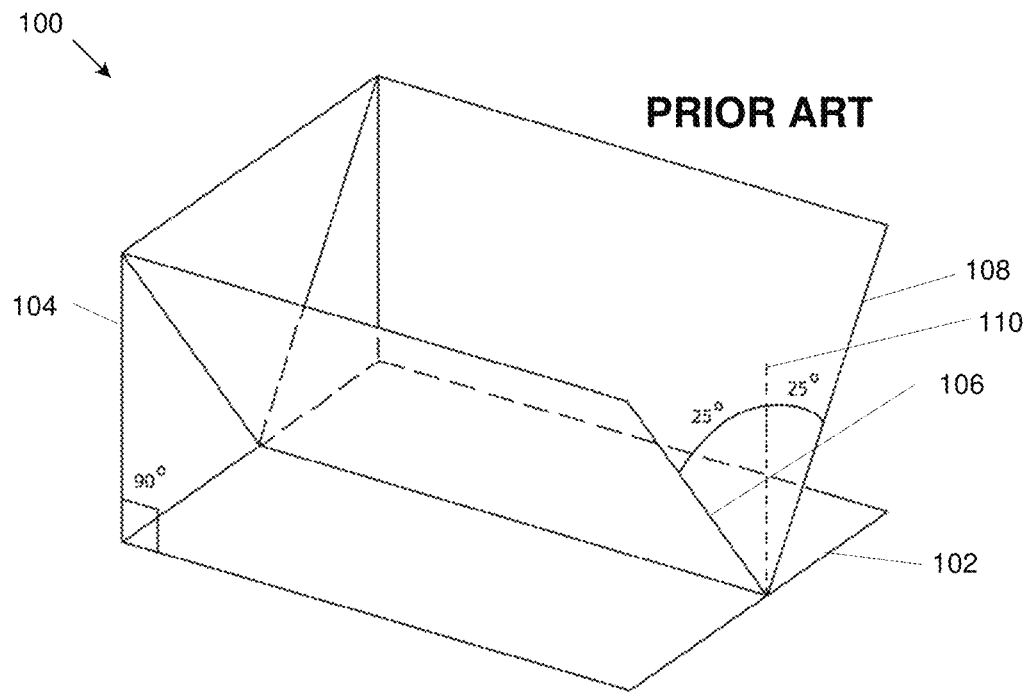
FIG. 1 illustrates a prior art positioning device.

A known prior art of an acrylic positioning mold or jig is illustrated in FIG. 1 and includes a transparent acrylic positioning device (100) consisting of four 4-mm-thick panels (102, 104, 106, 108) of radiolucent acrylic material, in the present example transparent polymethyl methacrylate. The first panel (102) forms a rectangular base, with the second panel (104) extending normally therefrom and from a short side thereof. The first and second panels (102, 104) support the third and fourth panels (106, 108), which are oriented to form a V-shape, and which diverge from a centre of the rectangular base, at 25° angles relative to a vertical and longitudinal plane through the base. The longitudinal plane lies on a centreline (110) extending from the centre of the rectangular base and in the same direction as the second panel (104).

The positioning device (100) is used to position an injured foot of a patient lying on a radiographic examination table in a supine position with their ankle maintained at a 90° angle relative to the leg and with the foot rotated inwardly at about 25°. The V-shape formed by the third and fourth panels (106, 108) receives the ankle and leg of the patient, and the sole of a foot of the patient may rest against the second panel (104). An X-ray image of the ankle may then be captured. As mentioned previously, the acrylic jig (100) does not provide for the taking of the AP mortise views at different inwardly rotated angular displacements of the foot at specific angles of less than the 25° and also does not provide for the taking of the calcaneal view of the ankle. In addition, the second foot of the patient has to be placed independently in the acrylic jig (100) in a separate procedure and X-ray images of the second foot may then be captured for comparative purposes. The divergent panels (106, 108) of the jig also extend up an appreciable height of the leg, namely about 500 mm.

Specific embodiments of the invention are now described in greater detail with reference to FIGS. 2 to 6. Like features and components are indicated by like reference numerals.

Figure 2:
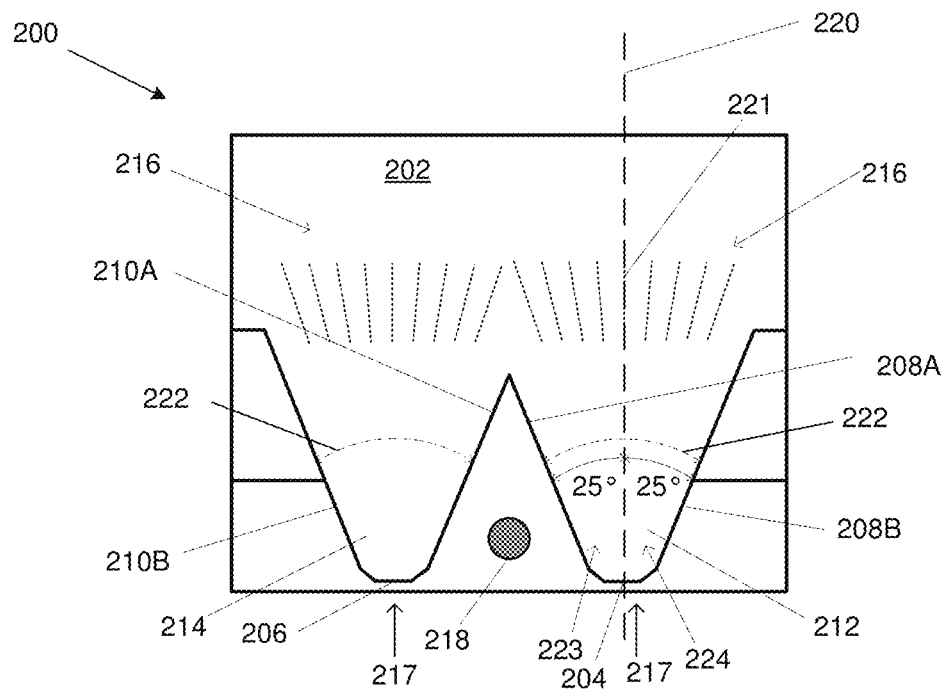
FIG. 2 illustrates an elevated view of an ankle imaging accessory according to a first embodiment of the invention.

An ankle imaging accessory (200) is shown in FIG. 2 in a first useable orientation and includes a substantially rectangular vertical wall (202) with a pair of spaced apart heel supports (204, 206) extending substantially normally from a longitudinal side of the wall. The wall comprises a pair of outwardly diverging stops (208A, 208B and 210A, 210B) extending integrally from each heel support (204, 206) and forming a right side heel support (206) and left side heel support (206). Together with each respective heel support, each pair of stops provides a V-shaped recess (212, 214) in which a patient's foot can be located.

Calibrations (216) indicating angular displacement of a foot between the stops are provided on the wall (202), and a calibration (217) indicating a calcaneal view may be provided adjacent each heel support and on an outer surface of the accessory (200). The calibrations (216) provided on the wall of the accessory are in 5° intervals relative to a vertical plane (220) through each heel support and range from 0° at the vertical plane to 25° at the pair of spaced apart stops on both sides of the vertical plane (220). The vertical plane (220) is seen directly from the side in FIG. 2, and appears as a line. The vertical plane extends through a centreline (221) of the heal support, also indicated by a calibration extending vertically from the heel support. The centreline for the right side heel support (204) is shown in FIG. 2, but it will be apparent that the left side heel support (206) includes a similar centreline. The accessory is, in this embodiment, moulded from an X-ray translucent plastics material, with the calibrations moulded into the material.

A sphere (218) of known diameter and made from an X-ray opaque material, in this embodiment steel, is moulded into the wall centrally between the heel supports and with its diameter inscribed on the wall. The known diameter of the sphere may be used as reference scale and may assist in ascertaining an ankle displacement of a fractured ankle of a patient.

Each pair of stops (208A and 208B, and 210A and 210B) define the limits of an arc (222) on which a foot pivoting within the heel supports (206, 204) may pivot. The arc of the present embodiment has a size of 25° in both an inward direction (223) and an outward direction (224) from the centreline (221), totalling 50°. Generally, the arc may be expected to have a maximum size of 25° in an inward direction relative to a centreline through the hell support, the centreline being parallel to a sagittal plane through the ankle imaging accessory.

Figure 3:
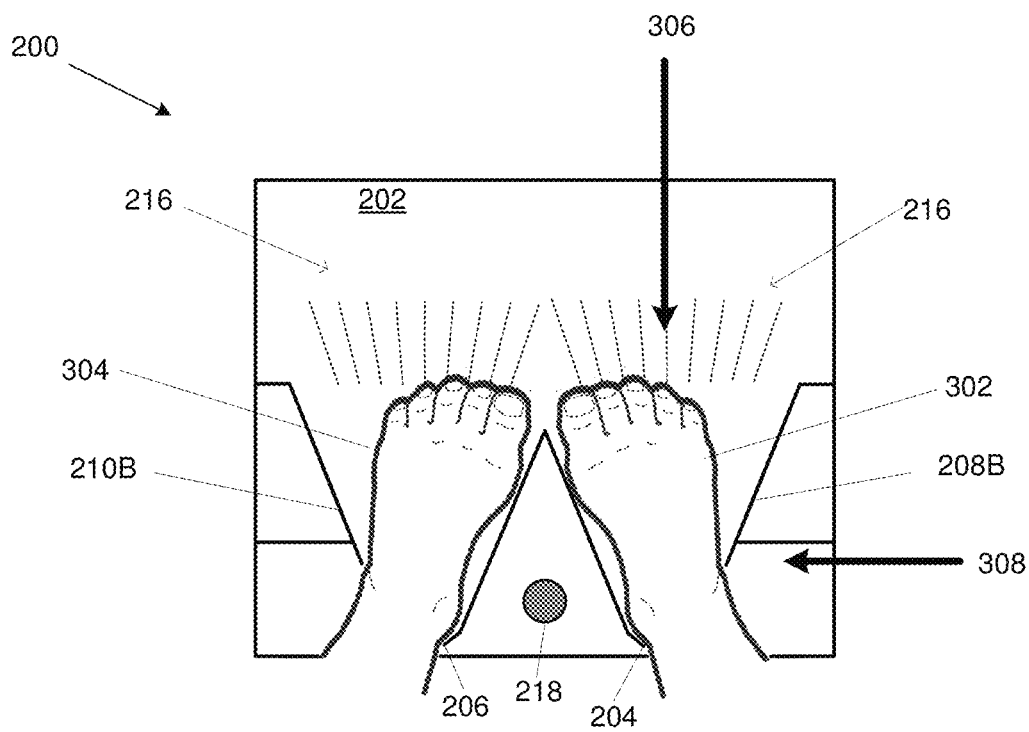
FIG. 3 illustrates placement of a patient's feet on the accessory of FIG. 2.
Figure 4:
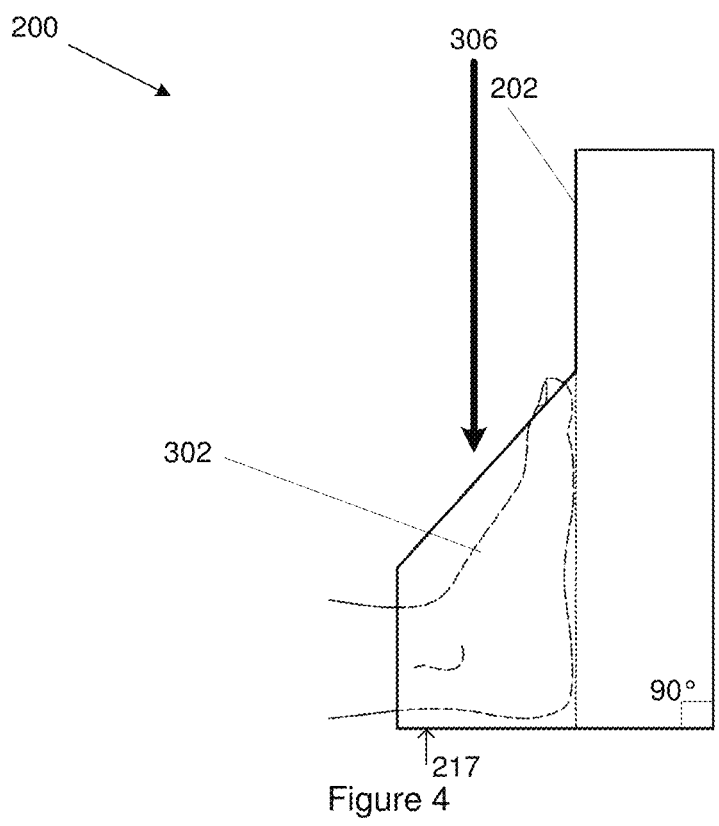
FIG. 4 is a side view illustrating the placement of a patient's feet on the accessory of FIG. 2.

FIGS. 3 and 4 show the ankle imaging accessory (200) in use in the first useable orientation. In use, a patient may be lying in a supine position on an X-ray bed or may be sitting with a leg extended horizontally and a foot (to be X-rayed may be placed within the appropriate V-shaped recess of the accessory. In FIG. 3, a right foot (302) is shown placed within right-sided V-shaped recess (212), while a left foot (304) is placed in the left-hand side V-shaped recess (214). It will be apparent that this will be the general use of the left sided and right sided recesses.

The heels of the patient's feet will generally rest on the respective heel supports (204, 206) and their soles will generally rest against and be supported by the vertical rectangular wall (202), thereby enabling the feet (302, 304) to be maintained at a 90° angle relative to the leg, as shown in FIG. 4. It should be noted that both of the patient's feet need not be injured, but that one of the feet may serve as control measure for comparative purposes during radiography. A vertical X-ray beam may be directed perpendicularly to an anterior surface of the ankle, substantially parallel to the vertical wall (202) and the vertical plane (220). The direction of the X-ray beam is indicated by a directional arrow (306). The patient may then rotate the foot with or without the assistance of the radiographer and X-ray images of the fractured ankle at various angular displacements of the foot may be captured.

It is appreciated that generally, the most reliable X-ray for the assessment of ankle congruity is an anteroposterior (AP) view or mortise view of the ankle, in which the patient's foot is rotated inwards by approximately 20° while the foot is maintained at a 90° angle relative to the leg. This projects the medial and lateral malleoli without the projection of the talus over the medial and lateral malleolus. Further, some patients do not exactly have a 20° mortise and, for example, may have a 15° mortise as in the AP view of the hip. The calibrations provided on the wall of the accessory are therefore used to rotate the foot in order to take X-ray images at different angular displacements of the foot. For example, the X-ray image may be taken when the central plane of the foot is aligned with the vertical plane (220) through the heel support, as described above with reference to in FIG. 2. Subsequent X-ray images may then be taken when the foot is internally rotated by 5°, 10°, 15°, 20° and 25°. It will be apparent that the calibrations may assist in orientating the foot appropriately.

Positioning, and rotating the fractured foot as described above depicts lateral talofibular, central talotibial, and medial talotibial views of the ankle (that is the AP mortise view of the ankle, projecting 3 spaces of the ankle). It is appreciated that the lateral talofibular view could also be obtained by directing an X-ray beam horizontally as depicted by a directional arrow (308) in FIG. 3.

Figure 5:
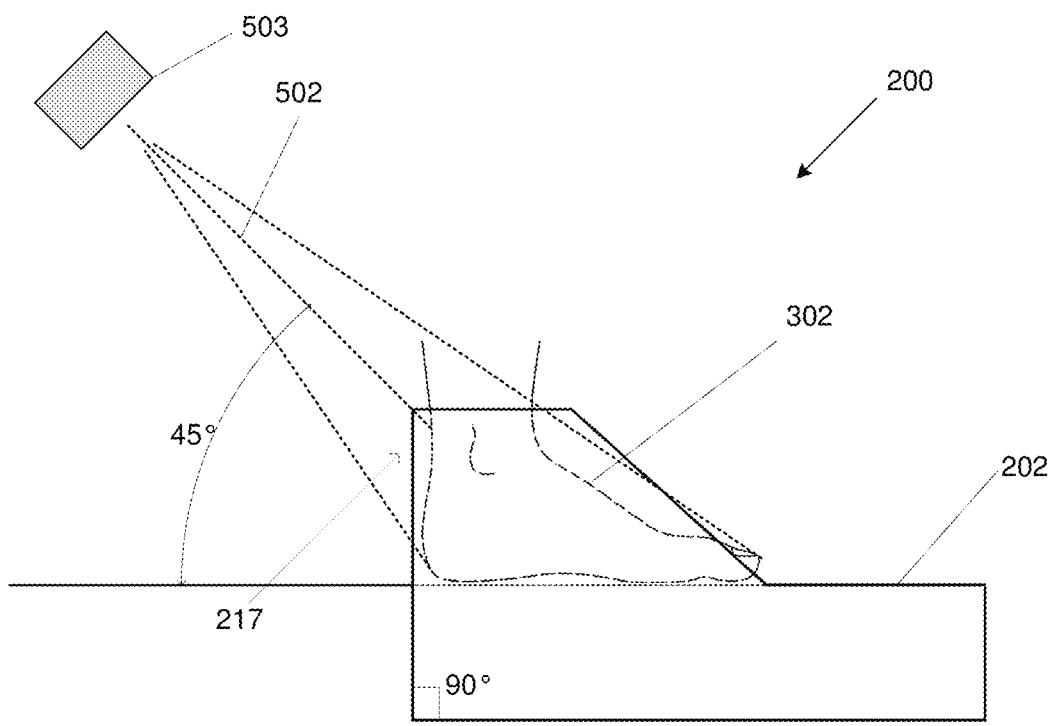
FIG. 5 is a side view of the ankle imaging accessory of FIG. 2 when used in an alternative orientation.

A calcaneal view of the ankle may be achieved by directing an X-ray beam along a 45° line through the posterior of the ankle. This is generally not achievable if the patient is in the supine position. As such, the accessory may then be oriented into a second usable orientation wherein the rectangular, formerly vertical wall (202) forms a horizontal base enabling the patient to stand on the accessory (200) with their feet (302, 304) within the respective V-shaped recesses (212, 214) of the accessory, as shown in FIG. 5. The calcaneal view is achievable with this setup and orientation. A direction of the X-ray beam for the calcaneal view is indicated by a line (502) extending from an X-ray device (503). The direction of the beam remains constant as it follows the path along the constant edge of the ankle imaging accessory.

Figure 6:
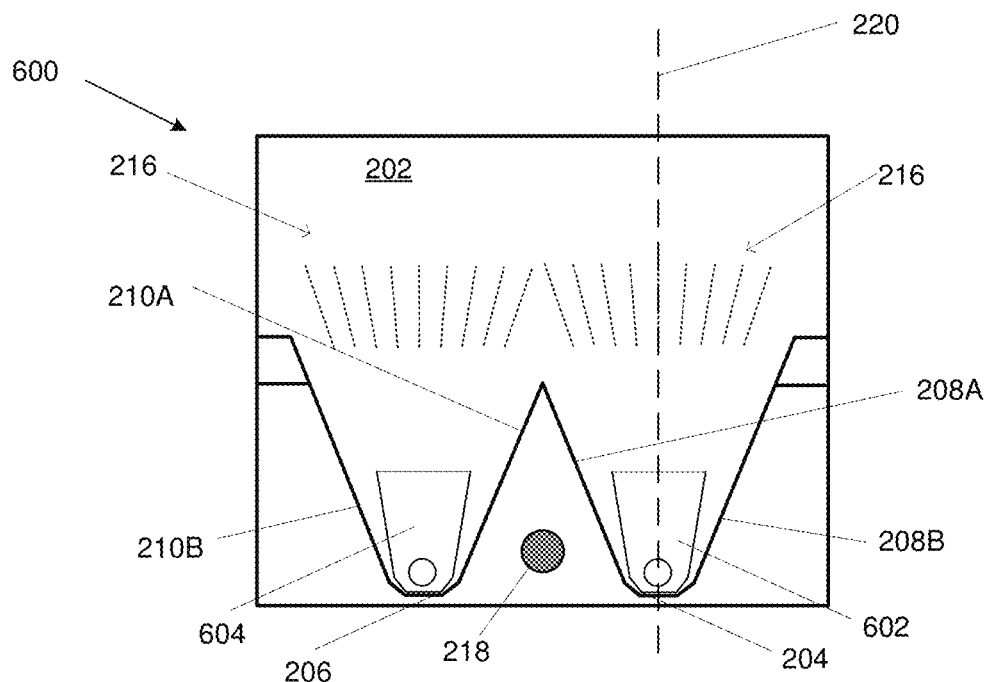
FIG. 6 illustrates an elevated view of the ankle imaging accessory according to a second embodiment of the invention.
Figure 7:
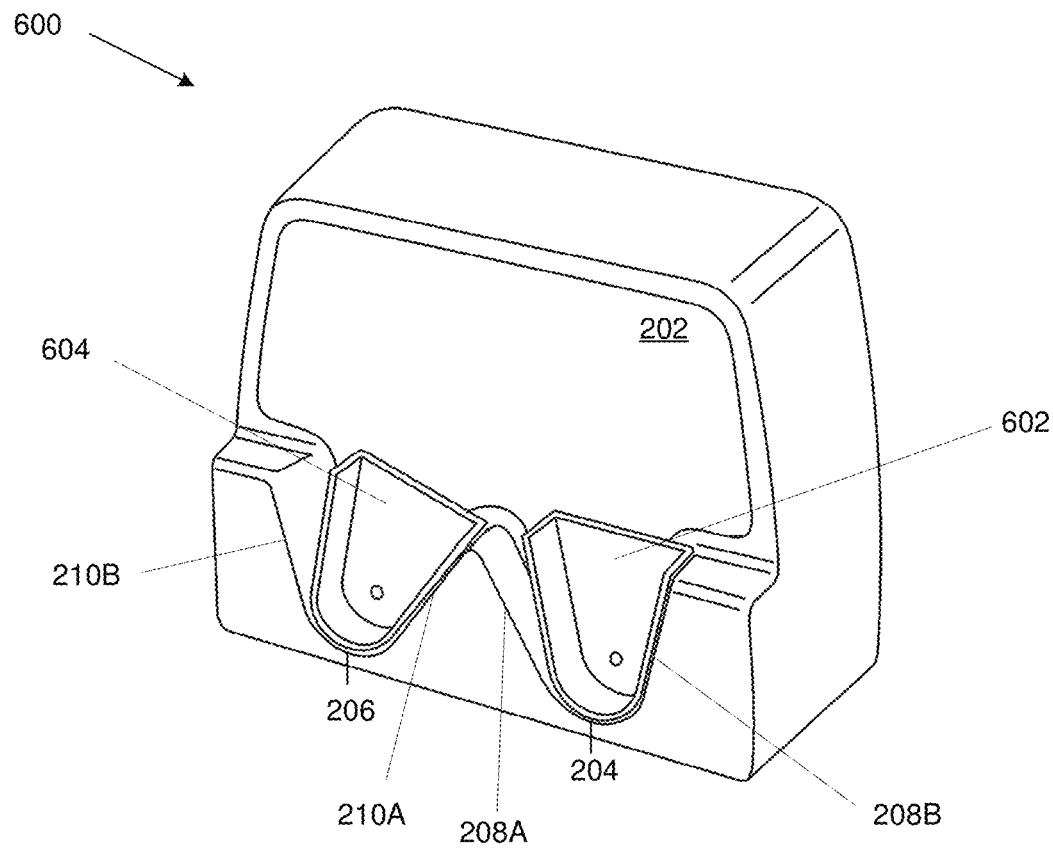
FIG. 7 is a three-dimensional view of the ankle imaging accessory of FIG. 6.

An alternative embodiment of the ankle imaging accessory (600) is shown in FIGS. 6 and 7. Components and features corresponding to the embodiment described with reference to FIGS. 2 to 5 are indicated by like reference numerals. The alternative embodiment includes heel pivoting devices (602, 604) which are pivotally secured to the rectangular wall at respectively a right heel support (204) and a left heel support (206).

Figure 8:
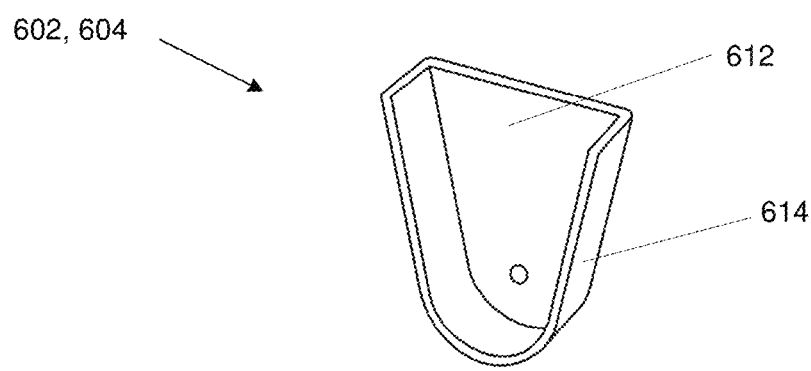
FIG. 8 illustrates a heel pivoting device of FIGS. 6 and 7.

A heel pivoting device (602, 604) is shown on its own in FIG. 8. Each heel pivoting device (602, 604) forms a partial container or "partial cup", and includes a base (612) in use lying substantially against the wall (202) of the accessory and a curved side wall (614) which extends substantially normally from the base (612). The side wall (614) does not extend all the way around the base, but provides an open-topped container where a user's foot may extend from the base (614), with only a heel of the patient's foot substantially held by the heel pivoting device. The side wall may abut its associated heel support in use. Each heel pivoting device (602, 604) is located within a V-shaped recess (212, 214) corresponding to respective heel supports (204, 206) of the accessory (600).

The pivotal connections between the heel pivoting devices (602, 604) and the accessory (600) allows heel pivoting devices to pivot between its associated pair of spaced apart stops (208A, 208B and 210A, 210B) and along an arc as described above. A patient's foot may be placed within an appropriate device (602, 604), and the angular displacement of the foot may be guided thereby as required for X-ray imaging purposes. The heel pivoting devices (602, 604) may simplify pivoting of a user's foot by either the user themselves or by the radiographer. The pivoting devices may be securable in the desired angular orientation, for example on indicated calibrations (216). The pivoting devices may also capture a user's heel to prevent unnecessary movement thereof whilst only allowing the desired angular pivoting.

The alternative embodiment may be used in substantially the same manner as the first embodiment described above, and may also be oriented between a first and second usable orientation.

It will be appreciated that the ankle imaging accessory may be of sufficient dimensions to fit a patient with up to a size 14 foot. However, heel pivoting devices may be provided in different sizes and may be interchangeable to allow for use with a matching foot size. It is further appreciated that the heel need not completely lie against the heel support, particularly with patients with wide feet. The accessory may be disposable and/or sterilisable and is made from an X-ray translucent material. The material may additionally be UV resistant, which may prevent degradation of the accessory from repeated radiation exposure.

Preferably, the imaging accessory is made from a plastic material. The plastic material renders the accessory relatively light, however, the accessory should still be sufficiently robust to sustain the weight of a patient and to give a stable support during radiography. Further, it is envisaged that edges and interior corners of the accessory may be rounded to prevent harm to the patient and/or medical practitioner, or tearing of surgical gloves during use. Radiography using the ankle imaging accessory of the present invention may produce better quality images as the variability associated with routine, freehand positioning of the ankle may be reduced or even eliminated.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

It is should be noted that the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

Throughout the specification unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. An ankle imaging accessory comprising a pair of heel supports for locating heels of a pair of feet, the heel supports extending substantially normal to a wall for supporting the heels, a pair of spaced apart stops extending from the wall in association with each heel support and which define the limits of an arc for a foot pivoting on the heel support, wherein the arc has a maximum size of 25° in at least an inward direction relative to a centreline through a heel support that is parallel to a sagittal plane through the ankle imaging accessory, and wherein the accessory is made from an X-ray translucent material.

2. The ankle imaging accessory as claimed in claim 1 wherein calibrations indicating selected angular displacements of a foot between the stops are provided on the wall.

3. The ankle imaging accessory as claimed in claim 1 wherein a calibration indicating a calcaneal view is provided adjacent each heel support.

4. The ankle imaging accessory as claimed in claim 1 wherein a heel pivoting device is pivotally secured to the wall at each heel support.

5. The ankle imaging accessory as claimed in claim 4 wherein each heel pivoting device is pivotable between its associated pair of stops.

6. The ankle imaging accessory as claimed in claim 1 including a sphere of an X-ray opaque material secured internally of the accessory.

7. The ankle imaging accessory as claimed in claim 6 wherein the diameter of the sphere is depicted on the accessory.

* * * * *